(12) United States Patent
Schuette et al.

(10) Patent No.: US 11,891,471 B2
(45) Date of Patent: Feb. 6, 2024

(54) FLEXIBLE POLYURETHANE FOAMS WITH HIGH WATER ABSORPTION CAPACITY

(71) Applicant: BASF SE, Ludwigshafen am Rhein (DE)

(72) Inventors: Markus Schuette, Lemfoerde (DE); Heinz-Dieter Lutter, Lemfoerde (DE); Anne Schubert, Lemfoerde (DE)

(73) Assignee: BASF SE, Ludwigshafen am Rhein (DE)

( * ) Notice: Subject to any disclaimer, the term of this patent is extended or adjusted under 35 U.S.C. 154(b) by 206 days.

(21) Appl. No.: 17/427,769

(22) PCT Filed: Jan. 31, 2020

(86) PCT No.: PCT/EP2020/052407
§ 371 (c)(1),
(2) Date: Aug. 2, 2021

(87) PCT Pub. No.: WO2020/161010
PCT Pub. Date: Aug. 13, 2020

(65) Prior Publication Data
US 2022/0106433 A1 Apr. 7, 2022

(30) Foreign Application Priority Data
Feb. 7, 2019 (EP) .................................... 19155983

(51) Int. Cl.
| | | |
|---|---|---|
| *A61F 13/00* | (2006.01) | |
| *A61L 26/00* | (2006.01) | |
| *C08G 18/10* | (2006.01) | |
| *C08G 18/30* | (2006.01) | |
| *C08G 18/48* | (2006.01) | |
| *C08G 18/76* | (2006.01) | |
| *C08J 9/02* | (2006.01) | |

(52) U.S. Cl.
CPC ........ *C08G 18/485* (2013.01); *A61L 26/0019* (2013.01); *A61L 26/0085* (2013.01); *C08G 18/10* (2013.01); *C08G 18/7671* (2013.01); *C08J 9/02* (2013.01); *C08G 2110/0008* (2021.01); *C08G 2110/0058* (2021.01); *C08G 2110/0066* (2021.01); *C08G 2110/0083* (2021.01); *C08J 2205/06* (2013.01); *C08J 2207/10* (2013.01); *C08J 2375/08* (2013.01)

(58) Field of Classification Search
None
See application file for complete search history.

(56) References Cited

U.S. PATENT DOCUMENTS

| | | | | |
|---|---|---|---|---|
| 4,365,025 A | * | 12/1982 | Murch | ............... C08G 18/7664 521/905 |
| 5,591,779 A | | 1/1997 | Bleys et al. | |
| 5,594,097 A | * | 1/1997 | Chaffanjon | ........ C08G 18/4837 528/68 |
| 2005/0176840 A1 | | 8/2005 | Chan et al. | |
| 2013/0261200 A1 | | 10/2013 | Doerr et al. | |

FOREIGN PATENT DOCUMENTS

| | | | | |
|---|---|---|---|---|
| EP | 2336211 A1 | | 6/2011 | |
| WO | 9429361 A1 | | 12/1994 | |
| WO | WO-9428044 A1 | * | 12/1994 | ............. C08G 18/10 |
| WO | 2004074343 A1 | | 9/2004 | |
| WO | 2012055834 A1 | | 5/2012 | |

OTHER PUBLICATIONS

European Search Report for EP Patent Application No. 19155983.0, dated Aug. 8, 2019, 3 pages.
International Search Report for corresponding PCT/EP2020/052407 dated Mar. 26, 2020, 2 Pages.

* cited by examiner

*Primary Examiner* — Melissa A Rioja
(74) *Attorney, Agent, or Firm* — Armstrong Teasdale LLP

(57) ABSTRACT

Described herein is a process for producing a hydrophilic flexible polyurethane foam. Also described herein is a flexible polyurethane foam obtainable by such a process and a method of using such a flexible polyurethane foam for treating wounds.

14 Claims, No Drawings

FLEXIBLE POLYURETHANE FOAMS WITH HIGH WATER ABSORPTION CAPACITY

CROSS-REFERENCE TO RELATED APPLICATIONS

This application is a U.S. National Phase Application of International Patent Application No. PCT/EP2020/052407, filed Jan. 31, 2020, which claims priority to European Patent Application No. 19155983.0, filed Feb. 7, 2019, the entire contents of which are hereby incorporated by reference herein.

FIELD OF INVENTION

The present invention relates to a process for producing a hydrophilic flexible polyurethane foam, in which (a) at least one polyurethane prepolymer having an isocyanate content of 5 to 10% by weight, based on the weight of the isocyanate prepolymer (a), is mixed with (b) at least one aqueous component in a ratio by weight of polyurethane prepolymer (a) to aqueous component (b) from 3:1 to 1:1.2 and allowed to react to form the flexible polyurethane foam, wherein the polyurethane prepolymer (a) is obtainable by mixing and reacting at least one isocyanate (a1) with at least one polyetherol (a2), the isocyanate (a1) comprises methylenediphenylene diisocyanate and the polyetherol (a2) has a hydroxyl number of 30 to 60 mg KOH/g and is obtainable by alkoxylating at least one difunctional and/or trifunctional starter molecule with ethylene oxide and propylene oxide and the ethylene oxide content, based on the total weight of alkylene oxide, is at least 60% by weight, based on the total weight of the polyether polyol (a2), wherein the polyetherol (a2) is obtainable by propoxylation of the starter molecule(s) in a first step up to a hydroxyl number of 400 to 1200 mg KOH/g, followed by an alkoxylation of the propoxylated starter molecule with a mixture of ethylene oxide and propylene oxide and finally an ethoxylation of the alkoxylation product thus obtained with 2 to 10% by weight ethylene oxide, based on the alkylene oxide used for producing the polyetherol (a2), and the aqueous component (b) comprises at least 90% by weight water (b1) and up to 10% by weight non-silicone-containing surface-active substances (b2). The present invention further relates to a flexible polyurethane foam obtainable by such a process and to the use of such a flexible polyurethane foam for treating wounds.

BACKGROUND

The use of hydrophilic flexible polyurethane foams for treating wounds is known and is described, for example, in WO 2012055834, WO 2004074343, EP 2336211 and WO 9429361.

WO 2012055834 and EP 2336211 disclose the production of hydrophilic flexible polyurethane foams starting from aliphatic isocyanates. For this purpose, an isocyanate prepolymer is reacted with an aqueous component. Disadvantages of such aliphatic isocyanates are their high volatility and thus the resulting health hazard during processing. Furthermore, aliphatic isocyanates are only weakly reactive during processing, which results in energy-intensive and slow processes. Acceleration by means of using catalysts is problematic because they can migrate out of the foam and such a foam would not be suitable for treating wounds.

WO 2004074343 and WO 9429361 describe hydrophilic flexible polyurethane foams which by reacting polyurethane prepolymers based on MDI and hydrophilic polyetherols with an aqueous component. However, the processes described in these documents result in flexible polyurethane foams with water absorption that can be improved in terms of the ab-solute amount of water absorbed and the water absorption rate, and also wet tensile strength that can be improved.

The object of the present invention, therefore, was to provide flexible polyurethane foams which are suitable for treating wounds, in which the mechanical properties, in particular the wet tensile strength, and the water absorption is further improved compared to known hydrophilic flexible polyurethane foams.

DESCRIPTION

The object according to the invention is achieved by a flexible polyurethane foam, obtainable by a process in which (a) at least one polyurethane prepolymer having an isocyanate content of 5 to 10% by weight, based on the weight of the isocyanate prepolymer (a), is mixed with (b) at least one aqueous component in a ratio by weight of polyurethane prepolymer (a) to aqueous component (b) from 3:1 to 1:1.2 and allowed to react to form the flexible polyurethane foam, wherein the polyurethane prepolymer (a) is obtainable by mixing and reacting at least one isocyanate (a1) with at least one polyetherol (a2), the isocyanate (a1) comprises methylenediphenylene diisocyanate and the polyetherol (a2) has a hydroxyl number of 30 to 60 mg KOH/g and is obtainable by alkoxylating at least one difunctional and/or trifunctional starter molecule with ethylene oxide and propylene oxide and the ethylene oxide content, based on the total weight of alkylene oxide, is at least 60% by weight, based on the total weight of the polyether polyol (a2), wherein the polyetherol (a2) is obtainable by propoxylation of the starter molecule(s) in a first step up to a hydroxyl number of 400 to 1200 mg KOH/g, followed by an alkoxylation of the propoxylated starter molecule with a mixture of ethylene oxide and propylene oxide and finally an ethoxylation of the alkoxylation product thus obtained with 2 to 10% by weight ethylene oxide, based on the alkylene oxide used for producing the polyetherol (a2), and the aqueous component (b) comprises at least 90% by weight water (b1) and up to 10% by weight non-silicone-containing surface-active substances (b2). The present invention further relates to a process for producing such a flexible polyurethane foam and to the use thereof for treating wounds.

The flexible foam according to the invention preferably has a density of 70 to 140 g/l, particularly preferably 80 to 120 g/l and especially 85 to 115 g/l. In the context of the present invention, the density was determined in accordance with Annex C of the European standard EN 14315-2. Furthermore, flexible polyurethane foams according to the invention preferably have a hardness of 1.0 to 5.0, particularly preferably 2.5 to 3.5. In the context of the present invention, the hardness was determined in accordance with Asker C ASTM D 2240.

The flexible polyurethane foams according to the invention are also characterized by an excellent water absorption capacity. This was determined as explained in the examples and is preferably more than 10 g per gram of foam, particularly preferably 12 to 20 g per gram of foam.

To produce the flexible polyurethane foam according to the invention, at least one polyurethane prepolymer (a) having an isocyanate content of 5 to 10% by weight, preferably 6 to 9% by weight and especially 6.5 to 8.5% by weight, based on the weight of the isocyanate prepolymer (a), is mixed with at least one aqueous component (b) and is reacted to form the polyurethane foam. The isocyanate content is known and can be determined, for example, by titration or spectrometrically. In the context of the invention, this is specified to the nearest 0.1% by weight.

The isocyanate prepolymer is obtained in this case by mixing and reacting at least one isocyanate (a1) with at least one polyetherol (a2).

The isocyanates (a) used are preferably aromatic di- and polyisocyanates; these are known in polyurethane chemistry and comprise, for example, isomers of toluene diisocyanate and isomeric and higher polycyclic homologs of methylenediphenylene diisocyanate. It is essential to the invention that the isocyanates comprise methylenediphenylene diisocyanate (a1). Methylenediphenylene diisocyanate (hereinafter also referred to as MDI) includes the isomers 2,2'-MDI, 2,4'-MDI and 4,4'-MDI. The proportion of 4,4'-methylenediphenylene diisocyanate is preferably 30 to 100% by weight and more preferably 45 to 90% by weight, particularly preferably 55 to 85% by weight, and the proportion of 2,4'-methylenediphenylene diisocyanate is 0 to 70% by weight and more preferably 10 to 55% by weight and particularly preferably 15 to 45% by weight, based in each case on the total weight of the isocyanate (a). In a particularly preferred embodiment, the isocyanate (a), based on the total weight of the isocyanates (a), comprises less than 10% by weight, preferably less than 5% by weight, and especially no isocyanates which are different from 4,4'-methylenediphenylene diisocyanate and 2,4'-methylenediphenylene diisocyanate. In particular, the isocyanate (a) comprises less than 1% by weight, preferably less than 0.01% by weight and more preferably no 2,2'-methylenediphenylene diisocyanate.

The polyetherols (a2) used are one or more polyetherols having a hydroxyl number of 30 to 60 mg KOH/g, preferably 35 to 50, which are obtainable by alkoxylating at least one difunctional and/or trifunctional starter molecule with ethylene oxide and propylene oxide, the ethylene oxide content, based on the total weight of alkylene oxide, is at least 60% by weight, preferably 65 to 95% by weight and particularly preferably 70 to 80% by weight, the propylene oxide content is greater than 0 to 40% by weight, preferably 5 to 35% by weight and particularly preferably 20 to 30% by weight. In the production of the polyetherol (a2), in addition to ethylene oxide and propylene oxide, less than 5% by weight and in particular no further alkylene oxides are preferably used.

Furthermore, according to the invention, the content of primary hydroxyl groups of the polyetherol (a2) is at least 90% by weight, preferably 95% by weight to 100% by weight, particularly preferably 99% by weight to 100% by weight and in particular 100%, based in each case on the total weight of the hydroxyl groups of the polyether polyol (a2).

The polyetherols (a2) can be produced by known processes, for example by anionic polymerization of alkylene oxides with addition of at least one starter molecule, which preferably comprises 2 to 4, particularly preferably 2 or 3, reactive hydrogen atoms in bonded form, in the presence of catalysts. Fractional functionalities can be obtained by using mixtures of starter molecules with different functionality. The nominal functionality ignores effects on functionality due by way of example to side reactions. Catalysts used may comprise alkali metal hydroxides, for example sodium hydroxide or potassium hydroxide, or alkali metal alkoxides, for example sodium methoxide, sodium ethoxide or potassium ethoxide or potassium isopropoxide, or in the case of cationic polymerization Lewis acids as catalysts, for example antimony pentachloride, boron trifluoride etherate or bleaching earth. It is also possible to use aminic alkoxylation catalysts, for example dimethylethanolamine (DMEOA), imidazole and imidazole derivatives. Catalysts used can moreover also comprise double-metal cyanide compounds, known as DMC catalysts.

Compounds containing hydroxyl groups or amine groups are suitable as starter molecules, for example ethylene glycol, diethylene glycol, glycerol, trimethylolpropane, pentaerythritol, methylamine, ethylamine, isopropylamine, butylamine, benzylamine, aniline, toluidine, toluenediamine (TDA), naphthylamine, ethylenediamine, diethylenetriamine, 4,4'-methylenedi-aniline, 1,3-propanediamine, 1,6-hexanediamine, ethanolamine, diethanolamine, and other dihydric or polyhydric alcohols or monoamines or diamines. The starter molecule for producing the polyetherol (a2) is preferably selected from the group consisting of ethylene glycol, diethylene glycol, propylene glycol, dipropylene glycol, glycerol, trimethylolpropane and mixtures thereof, particular preference being given to using glycerol, especially exclusively glycerol, as starter molecule.

The polyetherol (a2) according to the invention is obtainable by propoxylating a starter molecule in a first step up to a hydroxyl number of 400 to 1200 mg KOH/g, preferably 450 to 800 mg KOH/g, followed by an alkoxylation of the propoxylated starter molecule with a mixture of ethylene oxide and propylene oxide and by an ethoxylation of the alkoxylation product thus obtained with 2 to 10% by weight, preferably 3 to 5% by weight, ethylene oxide, based on the alkylene oxide used to produce the polyetherol (a2). It is essential to the invention that, after propoxylation of the starter molecule, it has on average at least one propylene oxide molecule. If starter molecules containing propylene oxide are already used, such as tripropylene glycol for example, this is considered as already propoxylated, but can be further propoxylated up to a hydroxyl number of 400 mg KOH/g. As a result, a polyetherol (a2) is obtained comprising an ethylene oxide end group comprising 2 to 10% by weight, preferably 3 to 5% by weight ethylene oxide, based on the total weight of the alkylene oxide used. It is not necessary in this case to purify the propoxylated starter molecule after propoxylation or the alkoxylation product of propoxylated starter molecule and the mixture of ethylene oxide and propylene oxide after alkoxylation and before ethoxylation. To follow the progress of the reaction, the conversion of the alkylene oxide can be monitored spectroscopically, for example by means of IR spectrometry. Before the addition of the final ethylene oxide, the conversion of alkylene oxide is preferably checked by means of spectroscopic methods so that essentially no unreacted propylene oxide is present in the reaction mixture. This means that the proportion of unreacted propylene oxide prior to addition of the ethylene oxide is less than 1% by weight, preferably less than 0.5% by weight, more preferably less than 0.1% by weight and especially less than 0.01% by weight, based on the total weight of the alkylene oxide used up to this time point.

The polyols (a2) according to the invention are preferably purified from any alkoxylation catalyst still present after production by bringing them into contact with an acidic ion exchange resin, for example Amberlite.

The alkali metal content of the polyol (a2) is preferably less than 50 ppm, particularly preferably less than 30 ppm and especially less than 20 ppm. The alkali metal content is usually measured in this case by means of titration.

In addition to the polyetherol (a2), it is preferred to use no further compounds having isocyanate-reactive groups for the production of the polyisocyanate prepolymer (a).

According to the invention, the aqueous component (b) used is a component comprising at least 90% by weight, preferably 94 to 100% by weight, particularly preferably 96 to 99.5% by weight and especially 97 to 99% by weight water (b1) and up to 10% by weight, preferably 0 to 6% by weight, particularly preferably 0.5 to 4% by weight and especially 1 to 3% by weight non-silicone, surface-active substances (b2).

The silicone-free surface-active substances (b2) are preferably compounds which are soluble in water at 20° C. to an extent of at least 5% by weight and which have isocyanate-reactive groups. At a concentration of 1% by weight in water at 20° C., the surface-active substances (b2) preferably reduce the surface tension by at least 10 mNm, particularly preferably by 15 mNm and especially by 20 mNm, measured according to DIN EN 14370: 2004-11. The surface-active substances are preferably alkylene oxide block copolymers having a molecular weight of 800 to 15 000 g/mol, preferably 1200 to 10 000 and especially 2000 to 8000 g/mol. The block copolymers particularly preferably have a central block of alkylene oxides having at least 3 carbon atoms, such as propylene oxide, butylene oxide, pentylene oxide and mixtures of such alkylene oxides, preferably propylene oxide, and two end blocks each of ethylene oxide. In this case, the ratio by weight of the central block to the end blocks is preferably from 1:0.5 to 1:5. Such surface-active substances are available under the trade name Pluriol® from BASF.

In addition to water (b1) and surface-active substances (b2)), the aqueous component (b) preferably does not comprise any compounds having isocyanate-reactive groups; component (b) particularly preferably does not comprise any amine catalysts and in particular no catalysts at all. In a further preferred embodiment, component (b) consists only of water (b1) and surface-active substances (b2).

To produce the hydrophilic flexible polyurethane foams according to the invention, polyurethane prepolymer (a) and aqueous component (b) are mixed. Mixing is preferably carried out at a ratio by weight of polyurethane prepolymer (a) to aqueous component (b) from 2.5:1 to 1.2:1, particularly preferably from 2.2:1 to 1.0:1 and especially 0.5:1 to 0.8:1. Mixing is preferably carried out at temperatures of the water component of greater than 0 to 25° C., preferably 1 to 10° C. and especially 3-5° C., and temperatures of the isocyanate component at preferably 10 to 50° C., particularly preferably 15 to 40° C. and especially 20-35° C. Curing is particularly preferably carried out in the absence of tertiary amines and, in particular, the mixture of polyisocyanate prepolymer and aqueous component (b) does not comprise any further substances.

The reaction mixture is preferably applied continuously to a release paper and cured, preferably in an oven. The application is usually carried out in layer thicknesses of 1 mm to 10 mm. After curing, the hydrophilic flexible polyurethane foam according to the invention is detached from the release paper.

The flexible polyurethane foam obtained according to the invention has a density of preferably 70 to 140 g/l, particularly preferably 80 to 120 g/l and especially 85 to 115 g/l and a water absorption capacity of at least 8 g/g, preferably at least 10 g/g and especially 12 to 20 g/g. The water absorption capacity is determined as follows: A solution of 142 mmol of sodium chloride and 2.5 mmol of calcium chloride in 1 liter of demineralized water was used (according to method EN 13726-12002 (solution 1).

From the foam to be tested, a foam sample 50 mm×50 mm in size is punched out from a 1.6 cm thick foam strip using a punch and immersed for 3 minutes in an aqueous test liquid according to EN 13726-1.2002 1. The foam is then carefully gripped at one corner without wringing it out, allowed to drain for 10 seconds and weighed again. The water absorption obtained (weight of foam after draining minus weight of the dry foam sample) is divided by the weight of the dry sample and reported in g/g. Furthermore, the polyurethane foam according to the invention also has a high rate of water absorption. To determine the water absorption rate on a dry foam sample, as is also used to determine the water absorption, 2 ml of the aqueous test liquid specified above is applied to the surface of the foam sample at room temperature and the time is stopped when it has been completely absorbed by the foam sample.

The polyurethane foam according to the invention also has very good mechanical properties, for example high tensile strength in the wet and in the dry state.

The hydrophilic flexible polyurethane foam according to the invention can preferably be used in the cosmetic field, for example as cosmetic pads or wound dressings, or as shoulder pads in items of clothing. Furthermore, the foam according to the invention can be used for passive climate regulation in closed spaces, for example in vehicles, such as automobiles, or buildings. It can also be used as a reversible liquid uptake, for example in serving trolleys. Furthermore, the foam according to the invention can be used as hearing protection or to absorb bodily fluids. The polyurethane foam according to the invention is particularly preferably used for wound treatment, for example as a wound dressing.

The present invention is illustrated below with the aid of examples.

The following substances were used:
Polyol 1: Glycerol-initiated polyether polyol having a hydroxyl number of 42 mg KOH/g, obtained by addition reaction of 6% by weight propylene oxide in a first step, a mixture of 69% by weight ethylene oxide and 20% by weight propylene oxide in a second step and 5% by weight ethylene oxide in a third step using KOH as catalyst.
Polyol 2: Diethylene glycol-initiated polyether polyol having a hydroxyl number of 42 mg KOH/g, obtained by addition reaction of 6% by weight propylene oxide in a first step, a mixture of 69% by weight ethylene oxide and 20% by weight propylene oxide in a second step and 5% by weight ethylene oxide in a third step using KOH as catalyst.
Polyol 3: Glycerol-initiated polyether polyol having a hydroxyl number of 32 mg KOH/g, obtained by alkoxylation of glycerol with a mixture of ethylene oxide and propylene oxide, available under the trade name Voranol® CP-1421 from Dow Chemicals.
Polyol 4: Glycerol-initiated block polyether polyol having a hydroxyl number of 42 mg KOH/g, obtained by addition reaction of 26% by weight propylene oxide in a first step, 74% by weight ethylene oxide in a second step using KOH as catalyst.
Auxiliary 1: Diglycol bis(chloroformate)
Auxiliary 2: Block copolymer composed of a central polyoxypropylene block having a molecular weight of 1750 g/mol and two terminal polyoxyethylene blocks each having a molecular weight of 350 g/mol
Auxiliary 3: Block copolymer composed of a central polyoxypropylene block having a molecular weight of 1750 g/mol and two terminal polyoxyethylene blocks each having a molecular weight of 1400 g/mol
Aqueous component: Mixture of 98% by weight water, 1% by weight auxiliary 2 and 1% by weight auxiliary 3
Iso 1: Mixture comprising 98.6% by weight 4,4'-MDI and 1.4% by weight 2,4'-MDI
Iso 2: Mixture of 2.4% by weight 2,2'-MDI, 48.6% by weight 2,4'-MDI and 49.0% by weight 4,4'-MDI Prepolymers were produced according to Table 1. For this purpose, the isocyanate was initially charged, the polymer was added dropwise with stirring and the mixture was stirred at 80° C. for one hour.

Unless otherwise stated, the quantities are given in parts by weight. The NCO content was determined in accordance with DIN EN ISO 14896.

The viscosity of the prepolymers was determined using a VT500 rotational viscometer from Haake in accordance with DIN EN ISO 3219.

TABLE 1

| | Pre-polymer | | | | | | | | | | |
|---|---|---|---|---|---|---|---|---|---|---|---|
| | 1 | 2 | 3 | 4 | 5 | 6 | 7 | 8 | 9 | 10 [1)] | 11 |
| NCO content | 8.7% | 12.2% | 6.3% | 4.6% | 12.1% | 8.2% | 6.5% | 4.6% | 8.3% | 7.2% | 8.3%** |
| Iso 1 [%] | 31.3 | 42 | 26 | 20.6 | | | | | 31.3 | 29 | 31.3 |
| Iso 2 | | | | | 42.1 | 31.3 | 26 | 20.6 | | | |
| Auxiliary 1 | 0.01 | 0.01 | 0.01 | 0.01 | 0.01 | 0.01 | 0.01 | 0.01 | 0.01 | 0.01 | 0.01 |
| Polyol 1 | 68.69 | 57.99 | 73.99 | 79.39 | 57.89 | 68.69 | 73.99 | 79.39 | | | |
| Polyol 2 | | | | | | | | | 68.69 | | |
| polyol 3 | | | | | | | | | | 70.99 | |
| Polyol 4 | | | | | | | | | | | 68.69* |

10 and 11 = comparative examples, Ex 11: polyol 4 is solid, m.p.: 35° C.

According to Tables 2 to 5, foams were produced from the prepolymers by mixing with an aqueous component, the procedure being as follows:

The water component is initially charged in a small PE beaker (V=160 mL) at room temperature. The isocyanate is initially charged in a prepared beaker (V=550 mL) at room temperature. The Vollrath stirrer is set to the lowest speed. A disposable stirrer having a diameter of 65 mm is used for mixing. The water component is now rapidly transferred to the trans-parent beaker with the isocyanate. When stirring starts, the stopwatch is also started. The starting materials are mixed with increasing speed until a homogeneous mixture is formed. The stirring time depends on the reactivity of the system and should be a maximum of 80% of the cream time.

TABLE 2

| | Example 1 | Example 2 | Example 3 | Example 4 | Example 5 | Example 6 | Example 7 |
|---|---|---|---|---|---|---|---|
| Aqueous component (1) | 15 | 18.75 | 25 | 30 | 37.5 | 45 | 50 |
| Prepolymer 1 (2) | 60 | 56.25 | 50 | 45 | 37.5 | 30 | 25 |
| Mixing ratio (1):(2) | 1:4 | 1:3 | 1:2 | 1:1.5 | 1:1 | 1:0.67 | 1:0.5 |
| Density [g/l] | 91 | 74 | 94 | 106 | 140 | 188 | 220 |
| Water absorption [g water per 1 g of foam] | 3.1 | 10.4 | 15.0 | 14.1 | 10.9 | 8.0 | 7.1 |

Table 2 shows that a mixing ratio of aqueous component (1) to prepolymer (2) of 1:1 results in the best water absorption capacities.

According to Tables 3 and 4, the aqueous component and the prepolymer were mixed in a ratio by weight of 1:2 to produce a foam. The NCO content of the isocyanate was varied in Table 3 and different polyols were used to produce the prepolymer in Table 4. Tables 3 and 4 specify the density and the water absorption capacity of the resulting foams.

TABLE 3

| | Example 8 | Example 9 | Example 10 | Example 11 | Example 12 | Example 13 | Example 14 | Example 15 |
|---|---|---|---|---|---|---|---|---|
| Aqueous component | 25 | 25 | 25 | 25 | 25 | 25 | 25 | 25 |
| Prepolymer 2, NCO = 12.2 | 50 | | | | | | | |
| Prepolymer 1 NCO = 8.7 | | 50 | | | | | | |
| Prepolymer 3 NCO = 6.3 | | | 50 | | | | | |
| Prepolymer 4 NCO = 4.6 | | | | 50 | | | | |

TABLE 3-continued

|  | Example 8 | Example 9 | Example 10 | Example 11 | Example 12 | Example 13 | Example 14 | Example 15 |
|---|---|---|---|---|---|---|---|---|
| Prepolymer 5 NCO = 12.1 |  |  |  |  | 50 |  |  |  |
| Prepolymer 6 NCO = 8.2 |  |  |  |  |  | 50 |  |  |
| Prepolymer 7 NCO = 6.5 |  |  |  |  |  |  | 50 |  |
| Prepolymer 8 NCO = 4.6 |  |  |  |  |  |  |  | 50 |
| Density [g/l] | 88 | 103 | 114 | 573* | 76 | 90 | 132 | 544 |
| Water absorption [g water per 1 g of foam] | 11.4 | 14.9 | 12.2 | 0.2 | 5.2 | 17.2 | 11.4 | 0.3 |

*coarse cell structure, very hard

Table 3 shows that optimum water absorption is obtained at an isocyanate content of the prepolymer of 6 to 9% by weight.

TABLE 4

|  | Example 16 | Example 17 | Example 18 | Example 19 |
|---|---|---|---|---|
| Aqueous component | 25 | 25 | 25 | 25 |
| Prepolymer 1 NCO = 8.7% | 50 |  |  |  |
| Prepolymer 9 NCO = 8.9% |  | 50 |  |  |
| Prepolymer 10 NCO = 7.2% |  |  | 50 |  |
| Prepolymer 11 NCO = 8.3% |  |  |  | 50 |
| Density [g/l] | 103 | 108 | 135 | 109 |
| Water absorption [g water per 1 g of foam] | 14.9 | 14.0 | 4.7 | 8.3 |

The invention claimed is:

1. A process for producing a hydrophilic flexible polyurethane foam, comprising mixing
   (a) at least one polyurethane prepolymer (a) having an isocyanate content of 5 to 10% by weight, based on the weight of the at least one polyurethane prepolymer (a), and
   (b) at least one aqueous component (b)
   in a ratio by weight of the at least one polyurethane prepolymer (a) to the at least one aqueous component (b) from 3:1 to 1:1.2 and allowing the mixture to react to form the flexible polyurethane foam,
   wherein the at least one polyurethane prepolymer (a) is obtained by mixing and reacting at least one isocyanate (a1) with at least one polyetherol (a2),
   wherein:
   the at least one isocyanate (a1) comprises methylenediphenylene diisocyanate,
   the at least one polyetherol (a2) has a hydroxyl number of 30 to 60 mg KOH/g and an ethylene oxide content of at least 60% by weight, based on the total weight of ethylene oxide and propylene oxide used to prepare the at least one polyetherol (a2), the at least one difunctional and/or trifunctional starter molecule in a first step up to a hydroxyl number of 400 to 1200 mg KOH/g, followed by an alkoxylation of the propoxylated starter molecule with a mixture of ethylene oxide and propylene oxide and finally an ethoxylation of the alkoxylation product thus obtained with 2 to 10% by weight ethylene oxide, based on the alkylene oxide used for producing the at least one polyetherol (a2), and
   the at least one aqueous component (b) comprises at least 90% by weight water (b1) and up to 10% by weight non-silicone-containing surface-active substances (b2), based in each case on the total weight of the at least one aqueous component (b).

2. The process according to claim 1, wherein the isocyanate content of the at least one polyurethane prepolymer (a) is 6 to 9% by weight, based on the weight of the at least one polyurethane prepolymer (a).

3. The process according to claim 1, wherein the at least one isocyanate (a1) comprises 30 to 100% by weight 4,4'-methylenediphenylene diisocyanate and 0 to 70% by weight 2,4'-methylenediphenylene diisocyanate, based in each case on the total weight of the at least one isocyanate (a1).

4. The process according to claim 1, wherein the at least one isocyanate (a1) comprises less than 10% by weight isocyanates which are different from 4,4'-methylenediphenylene diisocyanate and 2,4'-methylenediphenylene diisocyanate.

5. The process according to claim 1, wherein the at least one isocyanate (a1) comprises less than 1% by weight 2,2'-methylenediphenylene diisocyanate.

6. The process according to claim 1, wherein the ratio by weight of the at least one polyurethane prepolymer (a) to the at least one aqueous component (b) is from 2.5:1 to 1.2:1.

7. The process according to claim 1, wherein the at least one polyurethane prepolymer (a) and the at least one aqueous component (b) are reacted to form the flexible polyurethane foam in the absence of tertiary amines.

8. The process according to claim 1, wherein the at least one polyetherol (a2) has a primary hydroxyl group content of 95 to 100%.

9. The process according to claim 1, wherein the at least one difunctional and/or trifunctional starter molecule for producing the at least one polyetherol (a2) is selected from the group consisting of ethylene glycol, diethylene glycol, propylene glycol, dipropylene glycol, glycerol, trimethylolpropane and mixtures thereof.

10. The process according to claim 1, wherein the at least one polyetherol (a2) is obtained by propoxylation of the at least one difunctional and/or trifunctional starter molecule, wherein the propoxylated starter molecule has a hydroxyl number of 450 to 800 mg KOH/g, followed by an alkoxylation with a mixture of ethylene oxide and propylene oxide and an ethoxylation of the alkoxylation product thus obtained with 3 to 5% by weight ethylene oxide and propylene oxide, used to produce the at least one polyetherol (a2).

11. The process according to claim 1, wherein, in addition to the at least one polyetherol (a2), no further compounds with isocyanate-reactive groups are used to produce the at least one polyurethane prepolymer (a).

12. The process according to claim 1, wherein the density of the flexible polyurethane foam is 80 to 120 g/L.

13. A hydrophilic flexible polyurethane foam obtained by a process according to claim 1.

14. A method of treating a wound, comprising providing the hydrophilic flexible polyurethane foam according to claim 13 as a wound dressing.

* * * * *